United States Patent
Jikihara et al.

(10) Patent No.: US 9,040,747 B2
(45) Date of Patent: May 26, 2015

(54) METHOD FOR PRODUCING REDUCED COENZYME Q10, METHOD FOR STABILIZING SAME, AND COMPOSITION COMPRISING SAME

(75) Inventors: Takaaki Jikihara, Hyogo (JP); Takao Yamaguchi, Hyogo (JP); Shiro Kitamura, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 219 days.

(21) Appl. No.: 13/501,692

(22) PCT Filed: Oct. 15, 2010

(86) PCT No.: PCT/JP2010/068155
§ 371 (c)(1),
(2), (4) Date: Apr. 12, 2012

(87) PCT Pub. No.: WO2011/046199
PCT Pub. Date: Apr. 21, 2011

(65) Prior Publication Data
US 2012/0207731 A1    Aug. 16, 2012

(30) Foreign Application Priority Data
Oct. 16, 2009    (JP) ................. 2009-239754

(51) Int. Cl.
| | | |
|---|---|---|
| *A61K 38/43* | (2006.01) |
| *A23L 1/30* | (2006.01) |
| *A23L 1/00* | (2006.01) |
| *A23L 1/305* | (2006.01) |
| *A61K 9/10* | (2006.01) |
| *A61K 31/122* | (2006.01) |
| *A61K 47/10* | (2006.01) |
| *C07C 41/26* | (2006.01) |
| *C07C 41/46* | (2006.01) |

(52) U.S. Cl.
CPC ............ *A23L 1/30* (2013.01); *A23L 1/0029* (2013.01); *A23L 1/3051* (2013.01); *A23V 2002/00* (2013.01); *A61K 9/10* (2013.01); *A61K 31/122* (2013.01); *A61K 47/10* (2013.01); *C07C 41/26* (2013.01); *C07C 41/46* (2013.01)

(58) Field of Classification Search
None
See application file for complete search history.

(56) References Cited

U.S. PATENT DOCUMENTS

| | | | |
|---|---|---|---|
| 6,254,913 | B1 | 7/2001 | Wadsworth et al. |
| 8,124,139 | B2 * | 2/2012 | Yie et al. ............. 424/725 |
| 2006/0165672 | A1 | 7/2006 | Fujii et al. |
| 2010/0234643 | A1 | 9/2010 | Ueda et al. |

FOREIGN PATENT DOCUMENTS

| | | |
|---|---|---|
| JP | P2003-61588 | 3/2003 |
| JP | 2003-113129 A | 4/2003 |
| JP | 2007-526303 A | 9/2007 |
| WO | WO-2004/066988 A1 | 8/2004 |
| WO | WO-2005/092123 A1 | 10/2005 |
| WO | WO-2009/057611 A1 | 5/2009 |
| WO | WO-2009/136587 A1 | 11/2009 |

OTHER PUBLICATIONS

Database Caplus Chemical Abstracts Service, Columbus, Ohio, US; Database Accession No. 2009:856248, Abstract of DE 102008004090 Kohler et al. Jul. 16, 2009.*

* cited by examiner

*Primary Examiner* — Karl J Puttlitz
(74) *Attorney, Agent, or Firm* — Novak Druce Connolly Bove + Quigg LLP

(57) ABSTRACT

An object of the present invention is to provide a substance characterized by ability to reduce oxidized coenzyme Q10 and ability to stabilize reduced coenzyme Q10, which contains nutrients, has a favorable taste, and is excellent in general versatility, and a method for using the same. The present invention relates to a method for producing reduced coenzyme Q10 comprising reducing oxidized coenzyme Q10 with a particular amino acid. The present invention also relates to a method for stabilizing reduced coenzyme Q10 in the presence of a particular amino acid and a composition stabilized by the method.

7 Claims, No Drawings

METHOD FOR PRODUCING REDUCED COENZYME Q10, METHOD FOR STABILIZING SAME, AND COMPOSITION COMPRISING SAME

CROSS REFERENCE TO RELATED APPLICATIONS

This application is a National Phase filing under 35 U.S.C. §371 of PCT/JO2010/068155 filed on Oct. 15, 2010; and this application claims priority to Application No. 2009-239754 filed in Japan on Oct. 16, 2009 under 35 U.S.C. §119; the entire contents of all are hereby incorporated by reference.

TECHNICAL FIELD

The present invention relates to a method for producing reduced coenzyme Q10, a method for stabilizing reduced coenzyme Q10, and a composition comprising reduced coenzyme Q10. Reduced coenzyme Q10 is superior to oxidized coenzyme Q10 in terms of oral absorbability and, therefore, an excellent compound useful for foods (e.g., health food, food with nutrient function claims, and food for specified health use), supplements (e.g., dietary supplements), nutritive agents, beverages, feeds, animal drugs, cosmetics, pharmaceutical products, therapeutic agents, prophylaxes, and the like.

BACKGROUND ART

Reduced coenzyme Q10 is superior to oxidized coenzyme Q10 in terms of oral absorbability, and thus it is a compound that is very useful as an antioxidant. For example, reduced coenzyme Q10 can be obtained by carrying out a reduction reaction of oxidized coenzyme Q10 obtained by a conventionally known method comprising synthesis, fermentation, extraction from a natural product, or the like (Patent Literature 1).

Known examples of substances (reducing agents) effective for reduction of oxidized coenzyme Q10 to reduced coenzyme Q10 include sodium borohydride (Non-Patent Literature 1), sodium dithionite (Non-Patent Literature 2), sulfuric-acid-based substances (e.g., sodium sulfite) (Non-Patent Literature 3), and ascorbic acids (Patent Literature 2).

However, the above substances are compounds that need to be handled with care during manufacturing or use because of risk of ignition. In addition, they are expensive and problematic in terms of biological safety. Further, when they are used for foods, they negatively influence the flavors of foods. Thus, they do not always satisfy requirements. Therefore, in many cases, it is necessary to carry out a step of separating or removing such reducing agents and by-products thereof from reduced coenzyme Q10 after the end of a reduction reaction. Accordingly, there has been a strong need for a substance that can be used after a reduction reaction per se as reducing agent or by-product thereof effective for stabilization of reduced coenzyme Q10, and can be applied to foods (e.g., health foods), supplements, and the like.

As an aside, some substances effective for reduction of oxidized coenzyme Q10 can be used as substances effective for stabilization of reduced coenzyme Q10; i.e., as antioxidants. It is known that reduced coenzyme Q10 is readily oxidized by oxygen in the air so as to result in oxidized coenzyme Q10. Therefore, a method for stabilizing reduced coenzyme Q10 by protecting a preparation of reduced coenzyme Q10 or a compound drug containing reduced coenzyme Q10 from oxidation is very important.

Known examples of compounds effective for stabilization of reduced coenzyme Q10 include citric acid and ascorbic acids (Patent Literature 3). In addition, it is known that hydrocarbons, fatty acid esters, ethers, and nitriles are preferable as solvents for stabilizing reduced coenzyme Q10 (Patent Literature 4).

However, the above substances and solvents effective for stabilization of reduced coenzyme Q10 and by-products thereof do not necessarily meet requirements suitably since they may be problematic in terms of biological safety, negatively influence the flavors of foods when used for foods, and be expensive. In some cases, further stabilization of reduced coenzyme Q10 is needed.

In view of the background above, a substance which can be used to effectively reduce oxidized coenzyme Q10 and/or stabilize reduced coenzyme Q10, and which is inexpensive, functional, and unlikely to be dangerous when handled during manufacturing has strongly been needed.

CITATION LIST

Patent Literature

Patent Literature 1: JP Patent Publication (Kokai) No. 10-109933 A (1998)
Patent Literature 2: WO01/52822
Patent Literature 3: WO03/032967
Patent Literature 4: WO03/006408

Non-Patent Literature

Non-Patent Literature 1: Journal of Applied Toxicology, 28(1), 55-62, 2008
Non-Patent Literature 2: Pharmaceutical Research, 23(1), 70-81, 2006
Non-Patent Literature 3: Japanese Standards of Food Additives (7th edition)

SUMMARY OF INVENTION

Technical Problem

In view of the above, it is an object of the present invention to provide the following: a method for producing reduced coenzyme Q10 using a substance that is highly safe and thus can readily be applied to foods (e.g. health food, food with nutrient function claims, and food for specified health use), supplements (e.g., dietary supplements), nutritive agents, animal drugs, beverages, feeds, pet foods, cosmetics, pharmaceutical products, therapeutic agents, prophylaxes, and the like, and which need not be separated or removed from reduced coenzyme Q10 after production; an appropriate method for stabilizing such reduced coenzyme Q10 via protection from oxidation; and a stabilized composition.

Solution to Problem

As a result of intensive studies, surprisingly, the present inventors found that oxidized coenzyme Q10 can be reduced to reduced coenzyme Q10 in the presence of (a) particular amino acid(s), and that reduced coenzyme Q10 can be appropriately protected from oxidation caused by molecular oxygen in the presence of such particular amino acid(s). This has led to the completion of the present invention.

The present invention therefore relates to a method for producing reduced coenzyme Q10, which comprises reducing oxidized coenzyme Q10 using, as a substance effective for reduction of oxidized coenzyme Q10, an amino acid with a side chain containing a functional group comprising a nitrogen atom and/or an oxygen atom. The present invention further relates to a method for stabilizing reduced coenzyme Q10, which comprises allowing reduced coenzyme Q10 to coexist with an amino acid having a side chain containing a functional group comprising a nitrogen atom and/or an oxygen atom. The present invention further relates to a composition comprising reduced coenzyme Q10 and an amino acid with a side chain containing a functional group comprising a nitrogen atom and/or an oxygen atom.

This description includes part or all of the contents as disclosed in the description and/or drawings of Japanese Patent Application No. 2009-239754, which is a priority document of the present application.

Advantageous Effects of Invention

According to the present invention, a method for conveniently producing reduced coenzyme Q10, which comprises reducing oxidized coenzyme Q10 using a biologically safe substance, can be provided. In addition, a method for stabilizing reduced coenzyme Q10 using such substance can be provided. Also, such substance, which is effective for reduction of oxidized coenzyme Q10 and/or stabilization of reduced coenzyme Q10, can be expected to function as a nutrient. Therefore, the obtained composition of the present invention is very useful as, in particular, a product that is expected to provide various effects, such as a pharmaceutical product, a supplement, a food with nutrient function claims, a food for specified health use, a dietary supplement, a nutritive agent, an animal drug, a cosmetic, or a therapeutic agent.

DESCRIPTION OF EMBODIMENTS

The present invention is described in detail below. First, the method for producing reduced coenzyme Q10 of the present invention is described. The production method of the present invention is a method for producing reduced coenzyme Q10, which comprises reducing oxidized coenzyme Q10 using an amino acid with a side chain containing a functional group comprising a nitrogen atom and/or an oxygen atom.

Oxidized coenzyme Q10 used as a starting material in the production method of the present invention may be oxidized coenzyme Q10 alone or oxidized coenzyme Q10 in combination with reduced coenzyme Q10. If the oxidized coenzyme Q10 is used in combination with reduced coenzyme Q10, the proportion of the total amount of coenzyme Q10 (i.e., the sum of the amount of reduced coenzyme Q10 and the amount of oxidized coenzyme Q10) accounted for by the amount of oxidized coenzyme Q10 is, without limitation, for example, 1% by weight or more, generally 5% by weight or more, preferably 10% by weight or more, more preferably 20% by weight or more, and particularly preferably 50% by weight or more. The upper limit thereof is not particularly limited. However, if the oxidized coenzyme Q10 is used in combination with reduced coenzyme Q10, the above proportion is generally 99.9% by weight or less. Needless to say, oxidized coenzyme Q10 may account for 100% by weight of the total amount of coenzyme Q10; that is to say, oxidized coenzyme Q10 may be used alone. In addition, oxidized coenzyme Q10 used herein can be obtained by, for example, conventionally known methods including synthesis, fermentation, extraction from a natural product, or the like. Preferably, it is obtained via fermentation or extraction from a natural product.

The substance used for reduction of oxidized coenzyme Q10 in the production method of the present invention is an amino acid with a side chain containing a functional group comprising a particular hetero atom (hereinafter referred to as "amino acid used in the present invention" as well). The term "hetero atom" used herein refers to either a nitrogen atom or an oxygen atom. Therefore, for example, an amino acid with a side chain containing a functional group comprising a hetero atom used in the present invention is, but not limited to, an amino acid with a side chain containing a functional group comprising a nitrogen atom and/or an amino acid with a side chain containing a functional group comprising an oxygen atom.

If the hetero atom of a side chain of an amino acid of the present invention is a nitrogen atom; that is to say, if an amino acid with a side chain containing a functional group comprising a nitrogen atom is used as a substance for reducing oxidized coenzyme Q10 in the production method of the present invention, a "functional group comprising a nitrogen atom" includes, without limitation, an amino group, an amide group, an imino group, a guanidine group, an imidazole group, and an indole group. In addition, such "amino acid with a side chain containing a functional group comprising a nitrogen atom" may be a cyclic or acyclic amino acid. If it is a cyclic amino acid, a nitrogen atom may be shared between the functional group and the amino group of an amino acid. Specific examples thereof include lysine, arginine, tryptophan, proline, histidine, citrulline, asparagine, and glutamine. In view of the reducing ability to convert oxidized coenzyme Q10 into reduced coenzyme Q10, lysine, arginine, tryptophan, and proline are preferable and, further, lysine, arginine, and tryptophan are particularly preferable.

If the hetero atom of a side chain of an amino acid of the present invention is an oxygen atom; that is to say, if an amino acid with a side chain containing a functional group comprising an oxygen atom is used as a substance for reducing oxidized coenzyme Q10 in the production method of the present invention, a "functional group comprising an oxygen atom" includes, without limitation, a hydroxyl group, a carboxyl group, a carbonyl group, an ether group, and a phenol group. In addition, specific examples of an "amino acid with a side chain containing a functional group comprising an oxygen atom" include serine, tyrosine, threonine, aspartic acid, glutamic acid, asparagine, and glutamine. However, in view of the reducing ability to convert oxidized coenzyme Q10 into reduced coenzyme Q10, serine is particularly preferable.

Among the above amino acids used in the present invention, an amino acid with a side chain containing a functional group comprising a nitrogen atom is more advantageous in terms of ease of implementation of reduction reaction and production cost.

In addition, the amino acids described herein may be in any form. They may be in the form of a hydrate, salt, or derivative described below. Examples of a hydrate of an amino acid include a lysine hydrate and a lysine hydrochloride hydrate. In addition, examples of an amino-acid salt include: hydrochlorides such as lysine hydrochloride and arginine hydrochloride; sulfates such as tryptophan sulfate; sodium salts such as a lysine sodium salt; and potassium salts such as a lysine potassium salt. Examples of amino acid derivatives include an N-acyl amino acid. Further, amino acid derivatives also may include a polypeptide or protein comprising peptide-bound amino acids. Note that the absolute stereostructure of any amino acid described above is not particularly limited. Such amino acid may be in an L, D, or racemic form.

In addition, according to the production method of the present invention, the quantitative ratio of oxidized coenzyme Q10 and an amino acid of the present invention at the start of a reduction reaction is not particularly limited as long as it is effective for reduction of oxidized coenzyme Q10 to reduced coenzyme Q10. However, the equivalent amount of the amino acid(s) with respect to oxidized coenzyme Q10 is preferably 0.01 equivalent or more, more preferably 0.1 equivalent or more, and particularly preferably 1 equivalent or more. The upper limit of the amount of the amino acid(s) is not particularly limited. However, in consideration of production cost or efficacy as a nutrient, the amino acid(s) is(are) used in an amount of usually 1000 equivalents or less, preferably 500 equivalents or less, more preferably 250 equivalents or less, particularly preferably 100 equivalents or less, further preferably 50 equivalents or less, and most preferably 10 equivalents or less.

According to the production method of the present invention, the reaction system is not particularly limited and thus may be a homogeneous or inhomogeneous system as long as oxidized coenzyme Q10 used as a starting material and the amino acid(s) of the present invention are in contact with each other in the reaction system. For instance, each of oxidized coenzyme Q10 and the amino acid(s) of the present invention may exist in solid form being in contact with each other. Either oxidized coenzyme Q10 or the amino acid may exist in a liquid phase dissolved in a solvent or the like and the other may exist as a solid in said liquid phase. Oxidized coenzyme Q10 may exist in a molten form and the amino acid of the present invention may exist as a solid in the melt. Each of the oxidized coenzyme Q10 and the amino acid(s) may exist in liquid phases so that a liquid-liquid (double liquid) phase is formed. Further, oxidized coenzyme Q10 and the amino acid(s) may exist in a single liquid phase. Needless to say, a reaction system that enables a highly efficient contact between oxidized coenzyme Q10 and the amino acid of the present invention is effective for reduction of oxidized coenzyme Q10. In this regard, it is most preferable for oxidized coenzyme Q10 and the amino acid of the present invention to exist in a single liquid phase.

In view of the above, it is preferable to use a solvent so as to allow oxidized coenzyme Q10 and/or an amino acid of the present invention to exist in a liquid phase when a reduction reaction is carried out by the production method of the present invention. According to the production method of the present invention, the solvent used for a reduction reaction may be, without limitation, organic solvents such as hydrocarbons, fatty acid esters, ethers, alcohols, ketones, nitrogen compounds (e.g., nitriles and amides), sulfur compounds, fatty acids, and terpenes; fats; oils; and water. These solvents may be used alone or in combinations of two or more in the form of solvent mixture.

The hydrocarbons used herein include, without limitation, aliphatic hydrocarbon, aromatic hydrocarbon, and halogenated hydrocarbon. Aliphatic hydrocarbon and aromatic hydrocarbon are preferable. Of these, aliphatic hydrocarbon is particularly preferable.

Aliphatic hydrocarbon is not particularly limited and thus it may be cyclic or acyclic and saturated or unsaturated. However, it is particularly preferable to use acyclic aliphatic hydrocarbon. In addition, aliphatic hydrocarbon used herein is usually $C_3$-$C_{20}$ aliphatic hydrocarbon and preferably $C_5$-$C_{12}$ aliphatic hydrocarbon. Specific examples of aliphatic hydrocarbon include propane, butane, isobutane, pentane, 2-methylbutane, cyclopentane, 2-pentene, hexane, 2-methylpentane, 2,2-dimethylbutane, 2,3-dimethylbutane, methyl cyclopentane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, and dodecane. Of these, $C_5$-$C_8$ saturated aliphatic hydrocarbon is preferable. Particularly preferable examples thereof include pentane, 2-methylbutane, cyclopentane, hexane, 2-methylpentane, 2,2-dimethylbutane, 2,3-dimethylbutane, methylcyclopentane, cyclohexane, heptane, 2-methylhexane, 3-methylhexane, 2,3-dimethylpentane, 2,4-dimethylpentane, methylcyclohexane, octane, 2,2,3-trimethylpentane, isooctane, and ethylcyclohexane.

Aromatic hydrocarbon is not particularly limited. However, aromatic hydrocarbon used herein is usually $C_6$-$C_{20}$ aromatic hydrocarbon, preferably $C_6$-$C_{12}$ aromatic hydrocarbon, and particularly preferably $C_7$-$C_{10}$ aromatic hydrocarbon. Specific examples of aromatic hydrocarbon include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, and styrene. Aromatic hydrocarbon used herein is: preferably toluene, xylene, o-xylene, m-xylene, p-xylene, ethylbenzene, cumene, mesitylene, tetralin, butylbenzene, p-cymene, cyclohexylbenzene, diethylbenzene, or pentylbenzene; more preferably toluene, xylene, o-xylene, m-xylene, p-xylene, cumene, or tetralin; and most preferably cumene.

Halogenated hydrocarbon is not particularly limited and thus it may be may be cyclic or acyclic and saturated or unsaturated. However, in general, it is preferable to use acyclic halogenated hydrocarbon. Preferably, chlorinated hydrocarbon or fluorinated hydrocarbon is used. Particularly preferably, chlorinated hydrocarbon is used. Halogenated hydrocarbon used herein is preferably $C_1$-$C_6$ halogenated hydrocarbon, more preferably $C_1$-$C_4$ halogenated hydrocarbon, and particularly preferably $C_1$-$C_2$ halogenated hydrocarbon. Specific examples of halogenated hydrocarbon include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, and 1,1,1,2-tetrafluoroethane.

Halogenated hydrocarbon is: preferably dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, or 1,1,1,2-tetrafluoroethane; and more preferably dichloromethane, chloroform, 1,2-dichloroethylene, trichloroethylene, chlorobenzene, or 1,1,1,2-tetrafluoroethane.

The fatty acid esters used herein are not particularly limited. However, examples thereof include propionate, acetate, and formate. Among the fatty acid esters, acetate and formate are preferable, and acetate is particularly preferable. An ester group that can be preferably used herein is not particularly limited. However, it is usually $C_1$-$C_8$ alkyl ester or aralkyl ester, preferably $C_1$-$C_6$ alkyl ester, and more preferably $C_1$-$C_4$ alkyl ester.

Examples of propionate include methyl propionate, ethyl propionate, butyl propionate, and isopentyl propionate.

Examples of acetate include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and benzyl acetate. Acetate used herein is: preferably methyl acetate, ethyl acetate, propyl acetate, isopropyl acetate, butyl acetate, isobutyl acetate, sec-butyl acetate, pentyl acetate, isopentyl acetate, sec-hexyl acetate, or cyclohexyl acetate; more preferably methyl acetate, ethyl acetate, propyl acetate, isopropyl acetate, butyl acetate, or isobutyl acetate; and most preferably ethyl acetate.

Examples of formate include methyl formate, ethyl formate, propyl formate, isopropyl formate, butyl formate, isobutyl formate, sec-butyl formate, and pentyl formate. Formate is: preferably methyl formate, ethyl formate, propyl formate, butyl formate, isobutyl formate, or pentyl formate; and most preferably ethyl formate.

The ethers used herein are not particularly limited and thus they may be cyclic or acyclic and saturated or unsaturated. However, in general, it is preferable to use saturated ethers. Ethers used herein are usually $C_3$-$C_{20}$ ethers, preferably $C_4$-$C_{12}$ ethers, and particularly preferably $C_4$-$C_8$ ethers. Specific examples of ethers include diethyl ether, methyl-tert-butyl ether, dipropyl ether, diisopropyl ether, dibutyl ether, dihexyl ether, ethyl vinyl ether, butyl vinyl ether, anisole, phenetole, butyl phenyl ether, methoxytoluene, dioxane, furan, 2-methyl furan, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, and ethylene glycol dibutyl ether. Such ethers are: preferably diethyl ether, methyl-tert-butyl ether, dipropyl ether, diisopropyl ether, dibutyl ether, dihexyl ether, anisole, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether, and ethylene glycol monoethyl ether; more preferably diethyl ether, methyl-tert-butyl ether, anisole, dioxane, tetrahydrofuran, ethylene glycol monomethyl ether, and ethylene glycol monoethyl ether; further preferably diethyl ether, methyl-tert-butyl ether, and anisole; and most preferably methyl-tert-butyl ether.

The alcohols used herein are not particularly limited and thus they may be cyclic or acyclic and saturated or unsaturated. However, in general, it is preferable to use saturated alcohols. Alcohols used herein are usually $C_1$-$C_{20}$, preferably $C_1$-$C_{12}$, particularly preferably $C_1$-$C_6$, and further preferably C1-C5 monovalent alcohols. In addition, $C_2$-$C_5$ divalent alcohols or $C_3$ trivalent alcohols are preferable.

Examples of monovalent alcohols include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methyl-cyclohexanol, 2-methyl-cyclohexanol, 3-methyl-cyclohexanol, and 4-methyl-cyclohexanol. Monovalent alcohols used herein are: preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, and cyclohexanol; more preferably methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, and neopentyl alcohol; further preferably methanol, ethanol, 1-propanol, 2-propanol, 1-butanol, 2-butanol, isobutyl alcohol, 2-methyl-1-butanol, and isopentyl alcohol; and most preferably ethanol.

Examples of divalent alcohols include 1,2-ethanediol, 1,2-propanediol, 1,3-propanediol, 1,2-butanediol, 1,3-butanediol, 1,4-butanediol, 2,3-butanediol, and 1,5-pentanediol. Divalent alcohols are preferably 1,2-ethanediol, 1,2-propanediol, and 1,3-propanediol, and most preferably 1,2-ethanediol.

Glycerin and the like can be preferably used as trivalent alcohols.

The above ketones are not particularly limited. In general, $C_3$-$C_6$ ketones are preferably used. Specific examples of ketones include acetone, methylethyl ketone, methylbutyl ketone, and methylisobutyl ketone. Of these, acetone and methylethyl ketone are preferable, and acetone is most preferable.

The nitriles used herein are not particularly limited and thus they may be cyclic or acyclic and saturated or unsaturated. However, in general, it is preferable to use saturated nitriles. Nitriles used herein usually $C_2$-$C_{20}$ nitriles, preferably $C_2$-$C_{12}$ nitriles, and particularly preferably $C_2$-$C_8$ nitriles. Specific examples of nitriles include acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, cyanomethyl acetate, cyanoethyl acetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphthonitrile, biphenylcarbonitrile, phenylpropionitrile, phenyl butyronitrile, methylphenyl acetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenyl cyclohexanecarbonitrile, and tolylcyclohexanecarbonitrile. Nitriles are: preferably acetonitrile, propionitrile, succinonitrile, butyronitrile, isobutyronitrile, valeronitrile, cyanomethyl acetate, cyanoethyl acetate, benzonitrile, tolunitrile, and chloropropionitrile; more preferably acetonitrile, propionitrile, butyronitrile, and isobutyronitrile; and most preferably acetonitrile.

In addition to the above nitriles, examples of the nitrogen compounds used herein include nitromethane, acetonitrile, triethylamine, pyridine, formamide, N-methyl formamide, N,N-dimethyl formamide, N,N-dimethyl acetoamide, and N-methylpyrrolidone.

Examples of the sulfur compounds include dimethylsulfoxide and sulfolane.

Examples of the fatty acids used herein include formic acid, acetic acid, propionic acid, caprylic acid, capric acid, lauric acid, myristic acid, palmitic acid, stearic acid, isostearic acid, oleic acid, linoleic acid, linolenic acid, arachidonic acid, behenic acid, eicosapentaenoic acid, docosahexaenoic acid, and docosapentaenoic acid. However, fatty acids used herein are: preferably formic acid, acetic acid, caprylic acid, capric acid, oleic acid, linoleic acid, linolenic acid, arachidonic acid, eicosapentaenoic acid, docosahexaenoic acid, and docosapentaenoic acid; particularly preferably acetic acid, oleic acid, linoleic acid, linolenic acid, arachidonic acid, eicosapentaenoic acid, docosahexaenoic acid, and docosapentaenoic acid; further preferably oleic acid, linoleic acid, linolenic acid, eicosapentaenoic acid, and docosahexaenoic acid; and most preferably oleic acid.

The terpenes used herein are not particularly limited and thus they may be cyclic or acyclic and saturated or unsaturated. In general, terpenes such as hemiterpene, monoterpene, sesquiterpene, diterpene, triterpene, and tetraterpene can be used. Specific examples of terpenes include prenol, 3-methyl-3-butene-2-ol, tiglic acid, angelic acid, senecioic acid, isovaleric acid, alloocimene, α-bisabolene, bisabolene, β-bourbonene, δ-cadinene, δ-3-carene, α-caryophyllene, β-caryophyllene, p-cymene, dehydro-p-cymene, menthol, limonene, d-limonene, 1-limonene, cis-3,7-dimethyl-1,3,6,-octatriene, δ-elemene, β-elemene, α-farnesene, β-farnesene, farnesene, germacrene D, β-guaiene, longifolene, myrcene, β-ocimene, α-phellandrene, α-pinene, β-pinene, pinocamphone, sabinene, α-terpinene, γ-terpinene, terpinolen, thujopsis, valencene, α-copaene, hydrogenated limonene dimer, isocaryophyllene, pinene dimer, dipentene dimer, dipentene trimer, geraniol, citral, citronellal, citronellol, 1,8-cineole, hydroxycitronellal, linalool, cosmene, nerol, myrcenol, lavandulol, ipsdienol, neral, geranial, perylene, rose furan, geranyl acid, thioterpineol, α-terpineol, β-terpineol, γ-terpineol, δ-terpineol, carveol, terpin, perillaldehyde, perillyl alcohol, carvone, ascaridole, anethole, thujone, thujanol, α-ionone, β-ionone, γ-ionone, farnesol, nerolidol, α-sinensal, β-sinensal, bisabol, phytol, squalene, citronellyloxyacetaldehyde, myrtenal, perillaldehyde, 2-p-cymenol, 2-ethoxy-p-cymene, carvenol, 4-carvomenthenol, carvyl acetate, carvyl propionate, caryophyllene alcohol, caryophyllene alcohol acetate, 1,4-cineole, eugenol, d-selinene, thymol, d-camphene, and linalool acetate. Terpenes used herein are: preferably prenol, 3-methyl-3-butene-2-ol, tiglic acid, angelic acid, senecioic acid, isovaleric acid, alloocimene, α-bisabolene, bisabolene, β-bourbonene, δ-cadinene, δ-3-carene, α-caryophyllene, β-caryophyllene, p-cymene, dehydro-p-cymene, limonene, d-limonene, 1-limonene, cis-3,7-dimethyl-1,3,6,-octatriene, δ-elemene, β-elemene, α-farnesene, β-farnesene, farnesene, germacrene D, β-guaiene, longifolene, myrcene, β-ocimene, α-phellandrene, α-pinene, β-pinene, pinocamphone, sabinene, α-terpinene, γ-terpinene, terpinolen, thujopsis, valencene, α-copaene, hydrogenated limonene dimer, isocaryophyllene, pinene dimer, dipentene dimer, dipentene trimer, geraniol, citral, citronellal, citronellol, 1,8-cineole, hydroxy citronellal, linalool, nerol, myrcenol, neral, geranial, carvone, anethole, thujone, phytol, squalene, eugenol, d-selinene, thymol, and linalool acetate; particularly preferably α-bisabolene, bisabolene, δ-cadinene, α-caryophyllene, β-caryophyllene, limonene, d-limonene, 1-limonene, myrcene, α-phellandrene, α-pinene, β-pinene, α-terpinene, γ-terpinene, geraniol, citral, citronellol, 1,8-cineole, linalool, carvone, anethole, thujone, eugenol, d-selinene, thymol, and linalool acetate; and most preferably limonene and d-limonene.

In addition, essential oils containing the above terpenes can be used as solvents. Examples of essential oils include, but are not particularly limited to, orange oil, capsicum oil, mustard oil, garlic oil, caraway oil, clove oil, cinnamon oil, cocoa extract, coffee bean extract, ginger oil, spearmint oil, celery seed oil, thyme oil, onion oil, nutmeg oil, parsley seed oil, mentha oil, vanilla extract, funnel oil, pennyroyal oil, peppermint oil, eucalyptus oil, lemon oil, rose oil, rosemary oil, almond oil, ajowan oil, anise oil, amyris oil, angelica root oil, ambrette seed oil, estoragon oil, origanum oil, orris root oil, oribanum oil, cassia oil, cascarilla oil, cananga oil, chamomile oil, caramus oil, cardamon oil, carrot seed oil, cubeb oil, cumin oil, grapefruit oil, cinnamon leaf oil, cade oil, pepper oil, costus root oil, cognac oil, copaiba oil, coriander oil, Japanese basil oil, musk, juniper berry oil, star anise oil, sage oil, savory oil, geranium oil, tangerine oil, dill oil, neroli oil, tolu balsam oil, basil oil, birch oil, patchouli oil, palmarosa oil, pimento oil, petitgrain oil, bay leaf oil, bergamot oil, Peru balsam oil, gum benzoin, bois de rose oil, hop oil, boronia absolute, marjoram oil, mandarine oil, myrtle oil, yuzu (*Citrus junos*) fragrance, lime oil, lavandin oil, lavender oil, rue oil, lemongrass oil, lenthionine, lavage oil, laurel leaf oil, and wormwood oil.

Among the above organic solvents, alcohols, fatty acids, and terpenes are preferable. Alcohols are more preferable. Among alcohols, ethanol is most preferable.

The above fats or oils may be natural fats or oils from animals/plants, synthetic fats or oils, or modified fats or oils. Examples of plant fats and oils include coconut oil, palm oil, palm kernel oil, linseed oil, camellia oil, brown rice germ oil, rapeseed oil, rice oil, peanut oil, corn oil, wheat germ oil, soybean oil, perilla oil, cottonseed oil, sunflower seed oil, kapok oil, evening primrose oil, shea butter, sal butter, cocoa butter, sesame oil, safflower oil, olive oil, avocado oil, poppy seed oil, and burdock fruit oil. Examples of animal fats or oils include lard, milk fat, fish oil, and beef fat. Further, fats or oils (e.g., hydrogenated oil) obtained by processing the above fats or oils via separation, hydrogenation, or transesterification also can be used. Needless to say, medium-chain triglyceride (MCT), partial fatty acid glycerides, and the like can be used. In addition, mixtures of such fats and oils can be used. Examples of medium-chain triglyceride include, but are not particularly limited to, triglycerides comprising $C_6$-$C_{12}$ fatty acids and preferably triglycerides comprising $C_8$-$C_{12}$ fatty acids.

Among the above fats or oils, plant fats or oils, synthetic fats or oils, and modified fats or oils are preferable in terms of ease of handling, less probability of odor generation, and the like. Specifically, coconut oil, palm oil, palm kernel oil, rapeseed oil, rice oil, soybean oil, cottonseed oil, safflower oil, olive oil, medium-chain triglyceride (MCT), and partial fatty acid glycerides are preferable. Rice oil, soybean oil, rapeseed oil, safflower oil, medium-chain triglyceride, and partial fatty acid glycerides are particularly preferable. In terms of solubility of amino acids or the like, medium-chain triglyceride and partial fatty acid glycerides are most preferable.

Among the above solvents, solvents available for foods, pharmaceutical products, cosmetics, and the like are preferable. Solvents avaiable for foods are more preferable. In order to realize direct ingestion of an unprocessed reaction product or improve reactivity, solvents are preferably alcohols, water, fats, oils, fatty acids, terpenes, or mixtures thereof, and most preferably ethanol, water, or a solvent mixture containing ethanol and water.

The production method of the present invention is not limited as long as a reduction reaction is carried out while oxidized coenzyme Q10 used as a starting material and the amino acid(s) used as a reducing agent in the present invention are allowed to coexist in the solvent.

In addition, it is possible to add a surfactant to a reaction system during a reduction reaction according to the production method of the present invention. In many cases, it is preferable to add a surfactant.

Examples of surfactants used herein include, but are not limited to, glycerol fatty acid ester, sucrose fatty acid ester, organic acid monoglyceride, sorbitan fatty acid ester, polyoxyethylene sorbitan fatty acid ester, propylene glycol fatty acid ester, polyglycerol condensed ricinoleate, saponin, and phospholipid.

The glycerol fatty acid ester is not particularly limited. However, an example thereof is glycerol fatty acid ester with a degree of glycerol polymerization of 1 to 10. A fatty acid residue that constitutes glycerol fatty acid ester is not particularly limited and thus a $C_6$-$C_8$ fatty acid residue can be preferably used. Examples of fatty acid include caprylic acid, capric acid, lauric acid, myristic acid, palmitic acid, stearic acid, isostearic acid, oleic acid, linoleic acid, and linolenic acid.

The sucrose fatty acid ester is not particularly limited. However, an example thereof is sucrose fatty acid ester in which $C_6$-$C_{22}$ fatty acid is ester-bound to at least one hydroxyl group of sucrose. Examples thereof include sucrose laurate, sucrose myristate, sucrose palmitate, sucrose stearate, sucrose oleate, sucrose behenate, and sucrose erucate.

Examples of the organic acid monoglyceride include, but are not particularly limited to, monoglycerol caprylate succinate, monoglycerol stearate citrate, monoglycerol stearate acetate, monoglycerol stearate succinate, monoglycerol stearate lactate, monoglycerol stearate diacetyl tartrate, and monoglycerol oleate citrate.

The sorbitan fatty acid ester is not particularly limited. However, an example thereof is sorbitan fatty acid ester in which $C_6$-$C_{18}$ fatty acid is ester-bound to at least one hydroxyl group of sorbitan. Examples thereof include sorbitan monolaurate, sorbitan monopalmitate, sorbitan monostearate, and sorbitan monooleate. Examples of the polyoxyethylene sorbitan fatty acid ester include, but are not particularly limited to, polyoxyethylene sorbitan monopalmitate, polyoxyethylene sorbitan monostearate, polyoxyethylene sorbitan monooleate, polyoxyethylene sorbitan tristearate, and polyoxyethylene sorbitan trioleate, to each of which 6- to 20-mols of ethylene oxide chain is added.

The polyglycerol condensed ricinoleate is not particularly limited. However, an example thereof is polyglycerol condensed ricinoleate for which the average degree of polyglycerin polymerization is 2 to 10 and the average degree of polyricinoleic acid condensation (the average number of condensed ricinoleic acids) is 2 to 4. Examples thereof include tetrayglycerol condensed ricinoleate, pentaglycerol condensed ricinoleate, and hexaglycerol condensed ricinoleate.

As the propylene glycol fatty acid ester, either propylene glycol fatty acid monoester or propylene glycol fatty acid diester can be used. A fatty acid residue that constitutes propylene glycol fatty acid ester is not particularly limited. However, a $C_6$-$C_{18}$ fatty acid residue can be preferably used. Examples of fatty acid include caprylic acid, capric acid, lauric acid, myristic acid, palmitic acid, stearic acid, isostearic acid, oleic acid, linoleic acid, and linolenic acid.

Examples of the phospholipid include, but are not particularly limited to, egg yolk lecithin, purified soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramide phosphorylethanolamine, ceramide phosphorylglycerol, and mixtures thereof. Needless to say, phospholipids processed via hydrogenation, enzymatic degradation, or the like can be used. In view of the improvement of absorbability of reduced coenzyme Q10, it is preferable to use enzymatically degraded phospholipid.

Examples of the saponin include, but are not particularly limited to, enju saponin, quillaja saponin, purified soybean saponin, and yucca saponin.

According to the production method of the present invention, the concentration of oxidized coenzyme Q10 in a reaction system at the start of a reduction reaction (total weight of all reaction solutions) is not particularly limited. However, it is generally approximately 0.01% by weight or more, preferably approximately 0.1% by weight or more, more preferably approximately 0.2% by weight or more, particularly preferably approximately 1% by weight or more, further preferably approximately 2% by weight or more, and yet further preferably approximately 3% by weight or more.

The reaction temperature of a reduction reaction according to the production method of the present invention is not particularly limited. However, it is generally 20° C. or more, preferably 30° C. or more, more preferably 40° C. or more, further preferably 50° C. or more, particularly preferably 60° C. or more, and most preferably 75° C. or more.

In order to maximize the effects of the present invention, it is preferable to carry out the reduction reaction under, for example, a deoxygenated atmosphere. A deoxygenated atmosphere can be realized via substitution with inert gas, depressurization, boiling, or the combined use thereof. In any case, it is preferable to use an atmosphere generated via substitution with inert gas; that is to say, an inert gas atmosphere. Examples of inert gas include nitrogen gas, helium gas, argon gas, hydrogen gas, and carbon dioxide. Of these, nitrogen gas is preferable.

In the production method of the present invention, a reduction reaction may take place in a preparation. Specifically, the present invention encompasses production of reduced coenzyme Q10 by preparing a mixture comprising oxidized coenzyme Q10 and an amino acid of the present invention, processing the mixture into a preparation in a specific dosage form, and reducing oxidized coenzyme Q10 to reduced coenzyme Q10 in the preparation in such dosage form. In this case, reduction is induced after preservation for a certain period of time or longer or by heating, for example. According to the present invention, the dosage form of the preparation may be any of the following examples: capsules (hard capsules, soft capsules, or microcapsules), tablets, syrups, and dosage form for oral administration such as beverages, creams, suppositories, and toothpastes. In a case in which a reduction reaction is allowed to take place in a preparation, the preparation is preferably in a dosage form for oral administration, more preferably in the form of capsules, and particularly preferably in the form of soft capsules.

Reduced coenzyme Q10 can be readily produced by the production method of the present invention described above. Here, the proportion of the total amount of coenzyme Q10 (at the end of reaction) (i.e., the sum of the amount of reduced coenzyme Q10 and the amount of oxidized coenzyme Q10) accounted for by the amount of reduced coenzyme Q10 is usually approximately 10% by weight or more, preferably approximately 20% by weight or more, more preferably 30% by weight or more, particularly preferably 40% by weight or more, further preferably 50% by weight or more, even further preferably 60% by weight or more, and yet further preferably 80% by weight or more.

It is possible to obtain roughly purified or purified reduced coenzyme Q10 from reduced coenzyme Q10 obtained by the production method of the present invention via solvent removal, isolation, or purification after the end of a reduction reaction according to need. Alternatively, a mixed composition obtained after the end of a reduction reaction can be used directly as a composition comprising reduced coenzyme Q10 and the amino acid(s) or it can be processed into a preparation that can be used in the fields relating to pharmaceutical products, foods, and the like.

Next, the stabilization method of the present invention and the composition stabilized by the method of the present invention (hereinafter collectively referred to as "the stabilization method and the stabilized composition of the present invention") are described below. In the present invention, a composition comprising reduced coenzyme Q10 that is stable against oxidation can be obtained as a result of production of a composition in which reduced coenzyme Q10 coexists with the amino acid(s) of the present invention. Specifically, the stabilization method of the present invention is a method for stabilizing reduced coenzyme Q10, which comprises allowing reduced coenzyme Q10 to coexist with an amino acid with a side chain containing a functional group comprising a nitrogen atom and/or an oxygen atom. The composition of the present invention comprises reduced coenzyme Q10 and an amino acid with a side chain containing a functional group comprising a nitrogen atom and/or an oxygen atom.

According to the stabilization method and the stabilized composition of the present invention, reduced coenzyme Q10 to be stabilized may or may not be mixed with oxidized coenzyme Q10 in the composition. If the reduced coenzyme Q10 is mixed with oxidized coenzyme Q10, the proportion of the total amount of coenzyme Q10 (i.e., the sum of the amount of reduced coenzyme Q10 and the amount of oxidized coenzyme Q10) accounted for by the amount of reduced coenzyme Q10 is usually approximately 10% by weight or more, preferably approximately 20% by weight or more, more preferably 30% by weight or more, particularly preferably 40% by weight or more, further preferably 50% by weight or more, even further preferably 60% by weight or more, and yet further preferably 80% by weight or more. The upper limit thereof is not particularly specified. However, it is usually 99.9% by weight or less. Needless to say, reduced coenzyme Q10 may account for 100% by weight of the total amount of coenzyme Q10; that is to say, reduced coenzyme Q10 may be used alone.

Reduced coenzyme Q10 used in the stabilization method and the stabilized composition of the present invention can be obtained by, for example, a conventionally known method comprising synthesis, fermentation, extraction from a natural product, reduction of oxidized coenzyme Q10, or the like. Preferably, reduced coenzyme Q10 used in the stabilization method and the stabilized composition of the present invention is obtained by reducing oxidized coenzyme Q10 such as existing high-purity coenzyme Q10 or a mixture of oxidized coenzyme Q10 and reduced coenzyme Q10 with the use of a conventional reducing agent such as sodium hydrosulfite, sodium borohydride, or ascorbic acid. More preferably, it is obtained by oxidized coenzyme Q10 such as existing high-purity coenzyme Q10 or a mixture of oxidized coenzyme Q10 and reduced coenzyme Q10 obtained with the use of ascorbic acid. In addition, needless to say, reduced coenzyme Q10 obtained by the aforementioned production method of the present invention can be preferably used.

The amino acid(s) used in the stabilization method and the stabilized composition of the present invention is(are) "amino acid(s) with a side chain containing a functional group comprising a particular hetero atom," which is(are) the same as that(those) used in the aforementioned production method of the present invention. Specific examples and details thereof are the same as those described in connection with the production method of the present invention.

The quantitative ratio of reduced coenzyme Q10 and the amino acid(s) used in the stabilization method or contained in the stabilized composition of the present invention is not particularly limited. However, the amino acid(s) is(are) used in an amount of preferably 0.01 equivalent or more, more preferably 0.1 equivalent or more, and particularly preferably 1 equivalent or more with respect to oxidized coenzyme Q10. The upper limit of the amount of the amino acid(s) is(are) not particularly limited. However, in terms of economic efficiency, it is usually 1000 equivalents or less, preferably 500 equivalents or less, more preferably 250 equivalents or less, particularly preferably 100 equivalents or less, further preferably 50 equivalents or less, even further preferably 10 equivalents or less, and most preferably 5 equivalents or less.

According to the stabilization method and the stabilized composition of the present invention, reduced coenzyme Q10 and the amino acid(s) of the present invention coexist in a composition. The term "coexist" used herein refers to any form of contact therebetween. The contact form is not particularly limited. Here, the composition system may be a homogeneous or inhomogeneous system. For instance, reduced coenzyme Q10 and the amino acid(s) of the present invention may exist in a solid form when they are in contact with each other. Either reduced coenzyme Q10 or the amino acid(s) may exist in a liquid phase dissolved in a solvent or the like and the other may exist as a solid in said liquid phase. Reduced coenzyme Q10 may exist in a molten form and the amino acid(s) of the present invention can exist in a solid form in the molten substance. Reduced coenzyme Q10 and the amino acid(s) may separately exist in liquid phases so that a liquid-liquid (double liquid) phase is formed. Reduced coenzyme Q10 and the amino acid(s) may exist in a single liquid phase. Needless to say, a reaction system that enables a highly efficient contact between reduced coenzyme Q10 and the amino acid(s) of the present invention is effective for stabilization of reduced coenzyme Q10. In this regard, it is most preferable for reduced coenzyme Q10 and the amino acid(s) of the present invention to exist in a single liquid phase.

In view of the above, according to the stabilization method and the stabilized composition of the present invention, it is preferable to use a solvent so as to allow reduced coenzyme Q10 and/or the amino acid(s) of the present invention to exist in a liquid phase such that the solvent is contained in the composition and/or coexists with reduced coenzyme Q10 and/or the amino acid(s) of the present invention. According to the stabilization method and the stabilized composition of the present invention, the solvent used is not particularly limited. However, as described above for the production method of the present invention, examples thereof include organic solvents such as hydrocarbons, fatty acid esters, ethers, alcohols, ketones, fatty acids, terpenes, ketones, nitrogen compounds (including nitriles and amides), and sulfur compounds; fats; oils; and water.

Among the above solvents, solvents that can be used for foods, pharmaceutical products, cosmetics, and the like are preferable. Solvents that can be used for foods are particularly preferable. In consideration of direct digestion of a composition comprising reduced coenzyme Q10 and the amino acid(s), solvents are preferably alcohols, water, fats, oils, fatty acids, and terpenes, particularly preferably ethanol, water, fats, oils, fatty acids, terpenes, and mixtures thereof, most preferably ethanol, water, and a mixture of ethanol and water.

In addition to the above, specific types and preferable examples of solvents used in the stabilization method and the stabilized composition of the present invention are the same as those described in connection with the production method of the present invention.

In addition, it is also possible to add a surfactant in the stabilization method and the stabilized composition of the present invention in the same manner as in the case of the production method of the present invention. In addition, it is preferable to add a surfactant in many cases. Specific types and preferable examples of surfactants used in the stabilization method and the stabilized composition of the present invention are the same as those described in connection with the production method of the present invention.

According to the stabilization method and the stabilized composition of the present invention, a method for preparing a composition in which reduced coenzyme Q10 and the amino acid(s) of the present invention are allowed to coexist is not particularly limited. For example, when reduced coenzyme Q10 is externally added, reduced coenzyme Q10 may be simply mixed with the amino acid(s) of the present invention. Alternatively, it is possible to mix reduced coenzyme Q10 and the amino acid(s) of the present invention and then further mix the above solvent therewith. In addition, it is possible to mix the amino acid(s) of the present invention with a solution comprising the solvent containing reduced coenzyme Q10, mix reduced coenzyme Q10 with a solution comprising the solvent containing the amino acid(s) of the present invention, or mix a solution containing reduced coenzyme Q10 and a solution containing the amino acid(s) of the present invention.

Alternatively, reduced coenzyme Q10 obtained by the production method of the present invention can be directly used. That is to say, a mixture in which reduced coenzyme Q10 and the amino acid(s) coexist obtained after the completion of a reduction reaction can be directly used in the stabilization method and the stabilized composition of the present invention. This embodiment is one of the most preferable embodiments of the present invention.

According to the stabilization method and the stabilized composition of the present invention, the composition comprises reduced coenzyme Q10 and an amino acid of the present invention. In addition, if necessary, the composition may further contain a substance other than a solvent or surfactant. Examples of such substance include, but are not particularly limited to, an excipient, a disintegrating agent, a lubricant, a binder, a dye, an anti-aggregating agent, an absorption enhancer, a solubilizer, a stabilizer, an aroma chemical, and an active substance other than reduced coenzyme Q10.

The excipient is not particularly limited. However, examples thereof include sucrose, lactose, glucose, starch, dextrin, mannitol, crystalline cellulose, calcium phosphate, and calcium sulfate.

The disintegrating agent is not particularly limited. However, examples thereof include starch, agar, calcium citrate, calcium carbonate, sodium bicarbonate, dextrin, crystalline cellulose, carboxymethylcellulose, tragacanth, and alginic acid.

The lubricant is not particularly limited. However, examples thereof include talc, magnesium stearate, polyethylene glycol, silica, and hydrogenated oil.

The binder is not particularly limited. However, examples thereof include ethylcellulose, methylcellulose, hydroxypropylmethylcellulose, hydroxypropylcellulose, tragacanth, shellac, gelatine, pullulan, gum arabic, polyvinyl pyrrolidone, polyvinyl alcohol, polyacrylic acid, polymethacrylic acid, and sorbitol.

The dye is not particularly limited. However, examples thereof include titanium oxide, food dye, red iron oxide, safflower dye, caramel dye, gardenia dye, tar dye, and chlorophyll.

The anti-aggeregating agent is not particularly limited. However, examples thereof include stearic acid, talc, light anhydrous silicic acid, and hydrous silicon dioxide.

The absorption enhancer is not particularly limited. However, examples thereof include higher alcohols and higher fatty acids.

The solubilizer is not particularly limited. However, examples thereof include organic acids such as fumaric acid, succinic acid, and malic acid.

The stabilizer is not particularly limited. However, examples thereof include benzoic acid, sodium benzoate, ethyl p-hydroxybenzoate, beeswax, hydroxypropylmethylcellulose, and methylcellulose.

Examples of the aroma chemical include, but are not particularly limited to, orange oil, capsicum oil, mustard oil, garlic oil, caraway oil, clove oil, cinnamon oil, cocoa extract, coffee bean extract, ginger oil, spearmint oil, celery seed oil, thyme oil, onion oil, nutmeg oil, parsley seed oil, mentha oil, vanilla extract, funnel oil, pennyroyal oil, peppermint oil, eucalyptus oil, lemon oil, rose oil, rosemary oil, almond oil, ajowan oil, anise oil, amyris oil, angelica root oil, ambrette seed oil, estoragon oil, origanum oil, orris root oil, oribanum oil, cassia oil, cascarilla oil, cananga oil, chamomile oil, caramus oil, cardamon oil, carrot seed oil, cubeb oil, cumin oil, grapefruit oil, cinnamon leaf oil, cade oil, pepper oil, costus root oil, cognac oil, copaiba oil, coriander oil, Japanese basil oil, musk, juniper berry oil, star anise oil, sage oil, savory oil, geranium oil, tangerine oil, dill oil, citrus oil, tolu balsam oil, basil oil, birch oil, patchouli oil, palmarosa oil, pimento oil, petitgrain oil, bay leaf oil, bergamot oil, Peru balsam oil, gum benzoin, bois de rose oil, hop oil, boronia absolute, marjoram oil, mandarine oil, myrtle oil, yuzu (*Citrus junos*) fragrance, lime oil, lavandin oil, lavender oil, rue oil, lemongrass oil, lenthionine, lavage oil, laurel leaf oil, and wormwood oil.

Examples of the active component other than reduced coenzyme Q10 include vitamins, minerals, polyphenols, organic acids, sugars, peptides, and proteins.

The above substances may function in different ways. For example, starch may function not only as an excipient but also as a disintegrating agent.

According to the stabilization method and the stabilized composition of the present invention, the proportion of the total weight of the composition accounted for by the weight of the amino acid(s) of the present invention is not particularly limited. However, in order to maximize effects of stabilizing reduced coenzyme Q10, it is usually approximately 0.01% by weight or more, preferably approximately 0.1% by weight or more, more preferably approximately 1% by weight or more, further preferably 5% by weight or more, and particularly preferably approximately 10% by weight or more. The upper limit thereof is not particularly limited. However, in terms of economic efficiency or efficacy of the amino acid as a nutrient, it is usually approximately 70% by weight or less, preferably approximately 50% by weight or less, and more preferably approximately 30% by weight or less.

According to the stabilization method and the stabilized composition of the present invention, the proportion of the total weight of the composition accounted for by reduced coenzyme Q10 is not particularly limited. However, in order to allow reduced coenzyme Q10 in the composition to have certain efficacy, it is usually approximately 0.001% by weight or more, preferably approximately 0.01% by weight or more, more preferably approximately 0.1% by weight or more, and particularly preferably approximately 1% by weight or more. The upper limit thereof is not particularly limited. However, it is preferably approximately 50% by weight or less, more preferably approximately 30% by weight or less, and particularly preferably approximately 20% by weight or less.

In order to maximize the effects of the present invention, it is preferable to carry out the stabilization method of the present invention under, for example, a deoxygenated atmosphere. In addition, it is preferable to prepare and/or store the composition of the present invention under a deoxygenated atmosphere. In addition, it is preferable to process the composition into the above preparation or store the preparation after processing under a deoxygenated atmosphere. A deoxygenated atmosphere can be realized via substitution with inert gas, depressurization, boiling, or the combined use thereof. In any case, it is preferable to use an atmosphere generated via substitution with inert gas; that is to say, an inert gas atmosphere. Examples of inert gas include nitrogen gas, helium gas, argon gas, hydrogen gas, and carbon dioxide. Of these, nitrogen gas is preferable.

In addition, the composition of the present invention can be used per se. Alternatively, it can be used in the form of the preparation described above for the production method of the present invention. Specifically, it can be processed and used in the form of capsules (hard capsules, soft capsules, or microcapsules), tablets, a syrup, or a beverage for oral administration, a cream, a suppository, a toothpaste, or the like. Preferably, it is processed in the dosage form for oral administration. Particularly preferably, it is in the form of capsules. Most preferably, it is in the form of soft capsules. Upon processing treatment, a base material for capsules is not particularly limited. Examples of base materials that can be used include gelatines from beef bone, beef skin, pig skin, fish skin, and the like, and other base materials (e.g., carrageenan available as a food additive, seaweed-derived products such as alginic acid, plant-seed-derived products such as locust bean gum and guar gum, and manufacturing materials such as thickening agents and celluloses).

In the case of the composition of the present invention, reduced coenzyme Q10 used as an active ingredient is protected from oxidation and thus stably maintained. In addition, the amino acid(s) used for stabilization is(are) excellent in terms of biological safety and effective as nutrients. Thus, the composition of the present invention is safe and is expected to exhibit synergetic effects of such amino acid and reduced coenzyme Q10. Therefore, the composition of the present invention can be used as a composition useful for foods (e.g., food with nutrient function claims and food for specified health use), supplements, tonic drinks, pharmaceutical products, animal drugs, cosmetics, pet foods, and the like.

Further, when the composition of the present invention is produced by the production method of the present invention, not only can oxidized coenzyme Q10, which is an inexpensive product, be used as a starting material, but also the amino acid(s) used for reduction of oxidized coenzyme Q10, the biological safety of which having been verified, need not be separated nor removed after the end of the reduction reaction and further, the amino acid(s) of the present invention remaining in the composition can be used per se for stabilization of reduced coenzyme Q10. Therefore, the composition of the present invention is highly advantageous in terms of manufacturing. The use of the present invention enables in situ production of a composition comprising reduced coenzyme Q10, making it possible to reduce production costs for a composition comprising reduced coenzyme Q10. Accordingly, a composition comprising reduced coenzyme Q10 can be provided at a low price.

EXAMPLES

The present invention is hereafter described in greater detail with reference to the following examples, although the present invention is not limited thereto. The purity of reduced coenzyme Q10 and the weight ratio of reduced coenzyme Q10 to oxidized coenzyme Q10 were determined by HPLC analysis in the Examples. However, the limit value of the purity of reduced coenzyme Q10 of the present invention does not necessarily fall within the range of the obtained values of the purity. Similarly, the limit value of the weight ratio of reduced coenzyme Q10 to oxidized coenzyme Q10 does not necessarily fall within the range of the obtained values of the weight ratio. In the present Examples, for convenience, percentages are used to express the proportion of the total amount of coenzyme Q10 (the sum of the amount of oxidized coenzyme Q10 and the amount of reduced coenzyme Q10) accounted for by the amount of reduced coenzyme Q10, which is determined based on "the weight ratio of reduced coenzyme Q10 to oxidized coenzyme Q10." For instance, the phrase "the proportion of reduced coenzyme Q10 is 20% by weight" indicates that the weight ratio of reduced coenzyme Q10 to oxidized coenzyme Q10 is 20:80.

(HPLC Analysis Conditions)

Column: SYMMETRY C18 (Waters): 250 mm (length)×4.6 mm (inner diameter); mobile phase: $C_2H_5OH:CH_3OH=4:3$ (v:v); detection wavelength: 210 nm; flow rate: 1 ml/min; retention time for reduced coenzyme Q10: 9.1 min.; retention time for oxidized coenzyme Q10: 13.3 min.

Example 1

Crystalline oxidized coenzyme Q10 (0.3 g (i.e., 0.36 mmol)) was added to ethanol (4.5 g). One of the amino acids (6 equivalents (i.e., 2.16 mmol) each) listed in table 1 was separately added thereto. The obtained mixtures were stirred and heated at 78° C. for 16 hours under a nitrogen atmosphere. Table 1 shows HPLC analysis results regarding the proportions of reduced coenzyme Q10 (% by weight) determined after the reaction for the reaction solutions.

TABLE 1

| Example 1 | |
|---|---|
| | Proportion of reduced coenzyme Q10 (% by weight) |
| Arginine | 35% |
| Tryptophan | 21% |
| Lysine•n hydrate | 69% |
| Proline | 6% |
| Serine | 5% |

Example 2

Crystalline oxidized coenzyme Q10 (0.3 g (i.e., 0.36 mmol)) and tryptophan (6 equivalents (i.e., 2.16 mmol)) were added to a liquid mixture of Span 80 (0.4 g), glycerin (0.3 g), Tween 80 (4.9 g), and MCT (1.4 g). The obtained mixture was stirred and heated at 80° C. for 16 hours under a nitrogen atmosphere. Table 2 shows HPLC analysis results regarding the proportions of reduced coenzyme Q10 (% by weight) determined after the reaction for the reaction solution.

Comparative Example 1

Crystalline oxidized coenzyme Q10 (0.3 g (i.e., 0.36 mmol)) was added to a liquid mixture of Span 80 (0.4 g), glycerin (0.3 g), Tween 80 (4.9 g), and MCT (1.4 g). L-cysteine or N-acetylcysteine (6 equivalents (i.e., 2.16 mmol) each) was separately added thereto. The obtained mixtures were stirred and heated at 80° C. for 16 hours under a nitrogen atmosphere. Table 2 shows HPLC analysis results regarding the proportions of reduced coenzyme Q10 (% by weight) determined after the reaction for the reaction solutions.

TABLE 2

| | Proportion of reduced coenzyme Q10 (% by weight) |
|---|---|
| Example 2 | |
| Tryptophan | 33% |
| Comparative Example 1 | |
| L-cysteine | 7% |
| N-acetylcysteine | 3% |

Example 3

Crystalline oxidized coenzyme Q10 (0.3 g (i.e. 0.36 mmol)) was added to limonene (4.5 g). Proline (6 equivalents (i.e., 2.16 mmol)) or serine (6 equivalents (i.e. 2.16 mmol)) was separately added thereto. The obtained mixtures were stirred and heated at 85° C. for 16 hours under a nitrogen atmosphere. The reaction solutions were analyzed by HPLC after the reaction. As a result, the proportions of reduced coenzyme Q10 were found to be 8% by weight and 3% by weight, respectively.

Example 4

Crystalline oxidized coenzyme Q10 (0.3 g (i.e. 0.36 mmol)) and tryptophan (6 equivalents (i.e., 2.16 mmol)) were added to a liquid mixture of condensed ricinoleate (CR-310, Sakamoto Yakuhin Kogyo Co., Ltd.) (3.8 g) and MCT (3.8 g). The obtained mixture was stirred and heated at 80° C. for 16 hours under a nitrogen atmosphere. The reaction solution was analyzed by HPLC after the reaction. As a result, the proportion of reduced coenzyme Q10 was found to be 5% by weight.

Comparative Example 2

Crystalline oxidized coenzyme Q10 (0.3 g (i.e., 0.36 mmol)) was added to ethanol (4.5 g). One of the amino acids (6 equivalents (i.e., 2.16 mmol) each) listed in table 3 was separately added thereto. The obtained mixtures were stirred and heated at 78° C. for 16 hours under a nitrogen atmosphere. Table 3 shows HPLC analysis results regarding the proportions of reduced coenzyme Q10 (% by weight) determined after the reaction for the reaction solutions.

Comparative Example 3

Crystalline oxidized coenzyme Q10 (0.3 g (i.e., 0.36 mmol)) was added to a liquid mixture of Span 80 (0.4 g), glycerin (0.3 g), Tween 80 (4.9 g), and MCT (1.4 g). One of the amino acids (6 equivalents (i.e., 2.16 mmol) each) listed in table 3 was separately added thereto. The obtained mixtures were stirred and heated at 80° C. for 16 hours under a nitrogen atmosphere. Table 3 shows HPLC analysis results regarding the proportions of reduced coenzyme Q10 (% by weight) determined after the reaction for the reaction solutions.

Comparative Example 4

Crystalline oxidized coenzyme Q10 (0.3 g (i.e., 0.36 mmol)) was added to limonene (4.5 g). One of the amino acids (6 equivalents (i.e., 2.16 mmol) each) listed in table 3 was separately added thereto. The obtained mixtures were stirred and heated at 85° C. for 16 hours under a nitrogen atmosphere. Table 3 shows HPLC analysis results regarding the proportions of reduced coenzyme Q10 (% by weight) determined after the reaction for the reaction solutions.

Comparative Example 5

Crystalline oxidized coenzyme Q10 (0.3 g (i.e., 0.36 mmol)) was added to a liquid mixture of condensed ricinoleate (CR-310, Sakamoto Yakuhin Kogyo Co., Ltd.) (3.8 g) and MCT (3.8 g). One of the amino acids (6 equivalents (i.e., 2.16 mmol) each) listed in table 3 was separately added thereto. The obtained mixtures were stirred and heated at 80° C. for 16 hours under a nitrogen atmosphere. Table 3 shows HPLC analysis results regarding the proportions of reduced coenzyme Q10 (% by weight) determined after the reaction for the reaction solutions.

TABLE 3

Comparative Examples 2-5

| | Comparative Example 2 | Comparative Example 3 | Comparative Example 4 | Comparative Example 5 |
|---|---|---|---|---|
| Glycine | 0% | 0% | 0% | 1% |
| Valine | 1% | 0% | 0% | 0% |
| Isoleucine | 1% | 1% | 0% | 0% |
| Leucine | 0% | 0% | 0% | 1% |
| Alanine | 0% | 0% | 0% | 0% |

All publications, patents, and patent applications cited herein are incorporated herein by reference in their entirety.

The invention claimed is:

1. A method for producing reduced coenzyme Q10 which comprises reducing oxidized coenzyme Q10 at a reaction temperature or 50° C. or more using an amino acid with a side chain containing a functional group comprising a nitrogen atom and/or an oxygen atom, wherein the amino acid is lysine.

2. The production method of claim 1, wherein the reduction reaction is carried out in the presence of an organic solvent, a fat, an oil, water, or a mixture thereof.

3. The production method of claim 2, wherein the organic solvent is at least one member selected from the group consisting of alcohols, fatty acids, and terpenes.

4. The production method of claim 1, wherein the reduction reaction is allowed to take place in a preparation selected from the group consisting of capsules, tablets, syrups, and dosage form for oral administration.

5. The production method of claim 4, wherein the preparation is in the form of a capsule.

6. The production method of claim 1, wherein the reduction reaction is carried out under a deoxygenated atmosphere.

7. The production method of claim 1, wherein the reduction reaction is carried out in the presence of a solvent selected from the group consisting of alcohols, terpenes, plant fats and oils, medium-chain triglycerides (MCT) and mixtures thereof.

* * * * *